US006440703B1

(12) United States Patent
DeFrees

(10) Patent No.: US 6,440,703 B1
(45) Date of Patent: Aug. 27, 2002

(54) ENZYMATIC SYNTHESIS OF GANGLIOSIDES

(75) Inventor: Shawn DeFrees, San Marcos, CA (US)

(73) Assignee: Neose Technologies, Inc., Horsham, PA (US)

( * ) Notice: Subject to any disclaimer, the term of this patent is extended or adjusted under 35 U.S.C. 154(b) by 0 days.

(21) Appl. No.: 09/935,363

(22) Filed: Aug. 22, 2001

Related U.S. Application Data

(63) Continuation of application No. 09/203,200, filed on Nov. 30, 1998, now abandoned.
(60) Provisional application No. 60/067,693, filed on Dec. 1, 1997.

(51) Int. Cl.[7] .......................... C12P 19/26; C12P 19/18
(52) U.S. Cl. .............................. 435/84; 435/97; 435/74; 435/72
(58) Field of Search ............................. 435/97, 84, 74, 435/72

(56) References Cited

U.S. PATENT DOCUMENTS

| | | |
|---|---|---|
| 5,278,299 A | 1/1994 | Wong et al. |
| 5,627,271 A | 5/1997 | Flitsch et al. |

OTHER PUBLICATIONS

Constantino–Ceccarini, et al., "Effect of Exogenous Lipids on Membrane–Bound Ceramide Glycosyltransferases of Rat Brain", *Archives of Biochemistry and Biophysics* 1975, vol. 167, pp. 646–654.

Gaudino, et al., "A Novel and Efficient Synthesis of Neolacto Series Gangliosides 3'-nLM$_1$ and 6'-nLM$_1$" *J. Am. Chem. Soc.* 1994, vol. 116, pp. 1149–1150.

Guilbert, et al. "A Short Chemo–Enzymic Route to Glycosphingolipids Using Soluble Glycosyl Transferases" *J. Chem. Soc.* 1994, pp. 1181–1186.

Liu, et al. "A Striking Example of the Interfacing of Glycal Chemistry with Enzymatically Mediated Sialylation: A Concise Synthesis for GM$_3$" *J. Am. Chem. Soc.* 1993, vol. 115, pp. 4933–4934.

Schaeper, et al. "In vitro Biosynthesis of GbOse4Cer (globoside) and GM2 Ganglioside by the (1→3) and (→4)-N-acetyl β-D-galactosaminyltransferases from Embryonic Chicken Brain. Solubilization, Purification, and Characterization of the Transferases." *Carbohydrate Research* 1992, vol. 236, pp. 227–244.

Urban, et al. "Sequential Synthesis of Ganglioside Precursors Haematosides in Chicken Retina" *Biochemical Society Transactions* 1978, vol. 6, pp. 172–174.

Yanagisawa, et al. "Purification and Properties of G$_{M2}$ Synthase, UDP–N–acetylgalactosamine: G$_{M3}$ β-N-acetylgalactosaminyltransferase from Rat Liver" *Biochimica et Biophysica Acta* 1987 vol. 919, pp. 213–220.

Zehavi, et al. "Enzymic Glycosphingolipid Synthesis on Polymer Supports. III. Synthesis of G$_{M3}$ , its Analog [NeuNAcα(2–3)Galβ(1–4)Glcβ(1–3)Cer] and their lyso–derivatives" *Glycoconjugate Journal* 1998, vol. 15, pp. 657–662.

*Primary Examiner*—Francisco Prats
(74) *Attorney, Agent, or Firm*—Townsend and Townsend and Crew LLP

(57) ABSTRACT

This invention provides methods for practical in vitro synthesis of gangliosides and other glycolipids. The synthetic methods typically involve enzymatic synthesis, or a combination of enzymatic and chemical synthesis. One or more of the enzymatic steps is preferably carried out in the presence of an organic solvent.

18 Claims, 4 Drawing Sheets

ENZYMATIC SYNTHESIS OF GANGLIOSIDES

CROSS-REFERENCE TO RELATED APPLICATIONS

This application is a continuation of U.S. patent application Ser. No. 09/203,200 filed on Nov. 30, 1998 now abandoned and it claims the benefit of U.S. Provisional Application No. 60/067,693, filed Dec. 1, 1997, the disclosures of both of which are incorporated herein by reference in their entirety for all purposes.

BACKGROUND OF THE INVENTION

1. Field of the Invention

This invention pertains to the field of in vitro enzymatic synthesis of gangliosides and related compounds.

2. Background

Gangliosides are a class of glycolipids, often found in cell membranes, that consist of three elements. One or more sialic acid residues are attached to an oligosaccharide or carbohydrate core moiety, which in turn is attached to a hydrophobic lipid (ceramide) structure which generally is embedded in the cell membrane. The ceramide moiety includes a long chain base (LCB) portion and a fatty acid (FA) portion. Gangliosides, as well as other glycolipids and their structures in general, are discussed in, for example, Lehninger, *Biochemistry* (Worth Publishers, 1981) pp. 287–295 and Devlin, *Textbook of Biochemistry* (Wiley-Liss, 1992). Gangliosides are classified according to the number of monosaccharides in the carbohydrate moiety, as well as the number and location of sialic acid groups present in the carbohydrate moiety. Monosialogangliosides are given the designation "GM", disialogangliosides are designated "GD", trisialogangliosides "GT", and tetrasialogangliosides are designated "GQ". Gangliosides can be classified further depending on the position or positions of the sialic acid residue or residues bound. Further classification is based on the number of saccharides present in the oligosaccharide core, with the subscript "1" designating a ganglioside that has four saccharide residues (Gal-GalNAc-Gal-Glc-Ceramide), and the subscripts "2", "3" and "4" representing trisaccharide (GalNAc-Gal-Glc-Ceramide), disaccharide (Gal-Glc-Ceramide) and monosaccharide (Gal-Ceramide) gangliosides, respectively.

Gangliosides are most abundant in the brain, particularly in nerve endings. They are believed to be present at receptor sites for neurotransmitters, including acetylcholine, and can also act as specific receptors for other biological macromolecules, including interferon, hormones, viruses, bacterial toxins, and the like. Gangliosides are have been used for treatment of nervous system disorders, including cerebral ischemic strokes. See, e g., Mahadnik et al. (1988) *Drug Development Res.* 15: 337–360; U.S. Pat. Nos. 4,710,490 and 4,347,244; Horowitz (1988) *Adv. Exp. Med. and Biol.* 174: 593–600; Karpiatz et al. (1984) *Av. Exp. Med. and Biol.* 174: 489–497.

Certain gangliosides are found on the surface of human hematopoietic cells (Hildebrand et al. (1972) *Biochim. Biophys. Acta* 260: 272–278; Macher et al. (1981) *J. Biol. Chem.* 256: 1968–1974; Dacremont et al. *Biochim. Biophys. Acta* 424: 315–322; Klock et al. (1981) *Blood Cells* 7: 247) which may play a role in the terminal granulocytic differentiation of these cells. Nojiri et al. (1988) *J. Biol. Chem.* 263: 7443–7446. These gangliosides, referred to as the "neolacto" series, have neutral core oligosaccharide structures having the formula [Gal$\beta$-(1,4)GlcNAc$\beta$(1,3)]$_n$Gal$\beta$(1,4)Glc, where n=1–4. Included among these neolacto series gangliosides are 3'-nLM$_1$ (NeuAc$_\alpha$(2,3)Gal$\beta$(1,4) GlcNAc$\beta$(1,3)Gal$\beta$(1,4) Glc$\beta$(1,1)-Ceramide) and 6'-nLM$_1$ (NeuAc$\alpha$(2,6)Gal$\beta$(1,4)GlcNAc$\beta$(1,3)Gal$\beta$(1,4)-Glc$\beta$(1,1)-Ceramide).

The use of gangliosides as therapeutic reagents, as well as the study of ganglioside function, would be facilitated by convenient and efficient methods of synthesizing desired gangliosides. A combined enzymatic and chemical approach to synthesis of 3'-nLM$_1$ and 6'-nLM$_1$ has been described (Gaudino and Paulson (1994) *J. Am. Chem. Soc.* 116: 1149–1150). However, this and other previously available synthetic methods for ganglioside synthesis suffer from low efficiency and other drawbacks. Thus, a need exists for more efficient methods for synthesizing gangliosides. The present invention fulfills this and other needs.

SUMMARY OF THE INVENTION

The present invention provides methods for in vitro synthesis of glycosphingoids, including gangliosides, and other oligosaccharide-containing compounds. The methods involve the enzymatic transfer of carbohydrates, including sialic acids, to a sphingoid precursor. In particular, the methods involve contacting the sphingoid precursor with one or more glycosyltransferases and the corresponding sugar donor moiety for the glycosyltransferases, and other reactants required for glycosyltransferase activity, for a sufficient time and under appropriate conditions to transfer the sugar or sugars from the donor moiety to the sphingoid precursor. In some embodiments, one or more of the enzymatic reactions is carried out in the presence of an organic solvent, which increases the efficiency of the glycosylation reaction. The enzymatic step is typically preceded by hydrolysis of the fatty acid moiety from the ceramide; a fatty acid moiety can be reattached after completion of the glycosyltransferase reaction. As much as 100% efficiency is obtainable using the methods of the invention.

In one embodiment, the invention provides methods for adding one or more sialic acid residues to a glycosylated ceramide to form a ganglioside. The glycosylated ceramide is contacted with a sialyltransferase and a sialic acid donor moiety and other reactants required for sialyltransferase activity, under conditions such that sialic acid is transferred from the sialic acid donor moiety to the saccharide moiety of the glycosylated ceramide.

DETAILED DESCRIPTION

Definitions

Figure 1:
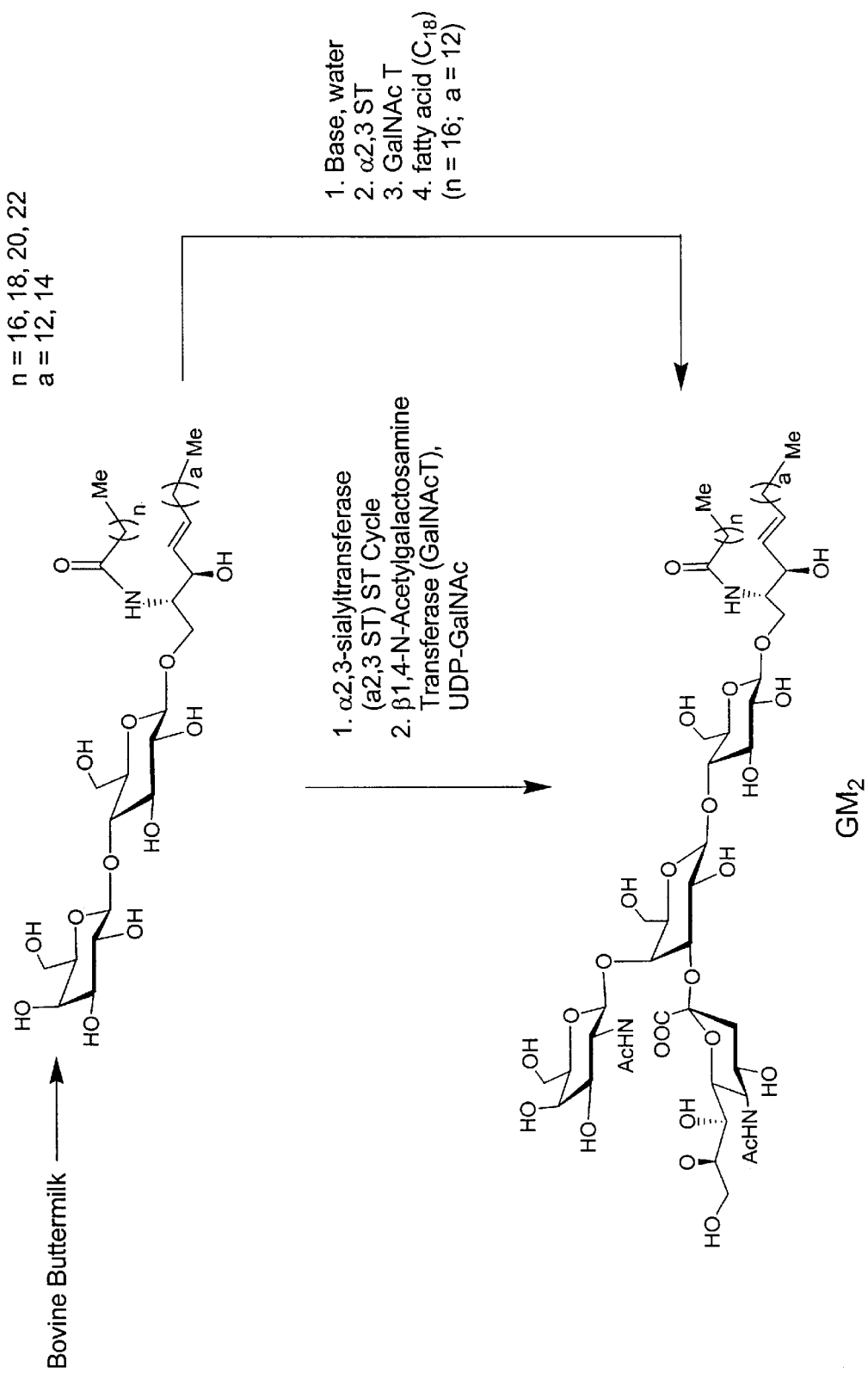
FIG. 1 shows a schematic diagram of two methods for synthesis of the ganglioside GM$_2$ by enzymatic synthesis using as the starting material lactosylceramide obtained from bovine buttermilk.

The following abbreviations are used herein:

Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (typically N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, 2-3, or (2,3). Each saccharide is a pyranose.

A "sphingoid," as used herein, includes sphingosines, phytosphingosines, sphinganines, ceramides, and the like. Both naturally occurring and synthetically produced compounds are included.

A "glycosphingolipid" is a carbohydrate-containing derivative of a sphingoid or ceramide. The carbohydrate residue is attached by a glycosidic linkage to O-1 of the sphingoid.

The term "sialic acid" (abbreviated "Sia") refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O—$C_1$–$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) Glycobiology 2: 25–40; *Sialic Acids: Chemistry, Metabolism and Function*, R. Schauer, Ed. (Springer-Verlag, New York (1992). The synthesis and use of sialic acid compounds in a sialylation procedure is described in, for example, international application WO 92/16640, published Oct. 1, 1992.

The term "isolated" is meant to refer to material which is substantially or essentially free from components which normally accompany the material as found in its native state. Thus, in some embodiments, the gangliosides and other glycosphingoids made using the methods of the invention do not include materials normally associated with in situ environment of these compounds. Typically, isolated glycoconjugates of the invention are at least about 80% pure, usually at least about 90%, and preferably at least about 95% pure as measured by band intensity on a silver stained gel or other method for determining purity. Purity or homogeneity can be indicated by a number of means well known in the art, such as are described below.

Description of the Preferred Embodiments

The present invention provides methods for efficient synthesis of glycolipids, including gangliosides, glycosphingoids, and other glycosylated structures. For example, the invention provides methods for synthesizing gangliosides that are useful for study of ganglioside biological function, as well as for therapeutic applications. The methods involve contacting a glycosylated or unglycosylated ceramide or sphingoid with a glycosyltransferase and a sugar donor moiety for a sufficient time and under appropriate reaction conditions to transfer the sugar from the donor moiety to the ceramide or sphingoid. In some embodiments, the enzymatic reaction is carried out in the presence of an organic solvent which can increase the efficiency of the reaction. In other presently preferred embodiments, the fatty acid moiety is removed from the ceramide or sphingoid prior to the glycosyltransferase reaction, thus further increasing the effectiveness of the enzymatic transfer.

A. Enzymatic Synthesis of Glycoceramide- and Sphingoid-Associated Oligosaccharides The invention provides methods of adding one or more saccharide moieties in a specific manner in order to obtain a desired ganglioside or other glycosphingolipid. The methods of the invention involve the use of one or more glycosyltransferases to synthesize glycosphingoids, including gangliosides and other glycosphingoids. Through use of a glycosyltransferase to link a desired carbohydrate to the precursor molecule, one can achieve a desired linkage with high specificity. In presently preferred embodiments, the methods of the invention involve the removal of the fatty acid moiety from the sphingoid precursor prior to the glycosyltransferase reaction, and/or the use of an organic solvent to facilitate the reaction.

The choice of glycosyltransferase(s) used in a given synthesis method of the invention will depend upon the acceptor which is used as the starting material and the desired end product. A method can involve the use of more than one glycosyltransferase, where more than one saccharide is to be added. The multiple glycosyltransferase reactions can be carried out simultaneously or sequentially. To obtain sufficient amounts of glycosyltransferase for large-scale reaction, a nucleic acid that encodes the enzyme can be cloned and expressed as a recombinant soluble enzyme by methods known to one of ordinary skill in the art.

In some embodiments, the invention allows one to synthesize a glycosphingolipid starting from a ceramide or other non-glycosylated sphingoid. The initial enzyme involved in synthesis of a glycoceramide from a ceramide precursor is, depending on the desired end product, either a ceramide glucosyltransferase (EC 2.4.1.80, for glucosylceramide) or a ceramide galactosyltransferase (EC 2.4.1.45, for galactosylceramide) (Step 1). For review of glycosphingolipid biosynthesis, see, e.g., Ichikawa and Hirabayashi (1998) *Trends Cell Biol.* 8:198–202. Accordingly, when the methods of the invention are used to synthesize a glycosphingolipid using a non-glycosylated ceramide or sphingoid as the starting material, the reaction mixture will include one of these enzymes. Ceramide glucosyltransferases are available from various sources. For example, the human nucleotide sequence is known (GenBank Accession No. D50840; Ichikawa et al. (1996) *Proc. Nat'l. Acad. Sci. USA* 93:4638–4643), so one can use recombinant methods to obtain the enzyme. The nucleotide sequence of the human ceramide galactosyltransferase also has been reported (GenBank Accession No. U62899; Kapitonov and Yu (1997) *Biochem. Biophys. Res. Commun.* 232: 449–453), and thus the enzyme is easily obtainable. The acceptor used in these reactions can be any of N-acylsphingosine, sphingosine and dihydrosphingosine. Suitable donor nucleotide sugars for the glycosyltransferase include UDP-Glc and CDP-Glc, while the galactosyltransferase typically uses UDP-Gal as a donor.

In other embodiments, an acceptor saccharide for a sialyltransferase or other glycosyltransferase is present on the precursor molecule to be modified upon in vivo synthesis of the precursor. For example, one can use as the starting material a glycosylceramide or other glycosphingoid. Such glycosphingoids can be sialylated or otherwise glycosylated using the methods of the invention to add additional saccharide residues to those that are already present on the precursor. In some embodiments, the additional saccharide residues are added without prior modification of the glycosylation pattern of the glycosphingolipid starting material. Alternatively, the invention provides methods of altering the glycosylation pattern of a glycosphingolipid prior to adding the additional saccharide residues. If the starting glycosphingolipid does not provide a suitable acceptor for the glycosyltransferase which catalyzes a desired saccharide addition, one can modify the glycosphingolipid to include an acceptor by methods known to those of skill in the art. For example, to provide a suitable acceptor for a sialyltransferase, a suitable acceptor can be synthesized by using a galactosyltransferase to attach a galactose residue to, for example, a GalNAc or other appropriate saccharide moiety that is linked to the glycosphingoid. In other embodiments, glycosphingoid-linked oligosaccharides can be first "trimmed," either in whole or in part, to expose either an acceptor for the sialyltransferase or a moiety to which one or more appropriate residues can be added to obtain a suitable acceptor. Enzymes such as glycosyltransferases and endoglycosidases are useful for the attaching and trimming reactions.

The second step in the synthesis of gangliosides involves the addition of a second carbohydrate residue, galactose, to the glucosylsphingoid to form the structure Galβ1-4Glc-R, wherein R is ceramide (and the product is lactosylceramide) or other sphingoid (Step 2). This reaction is catalyzed by a UDP-Gal: glucosylceramide β-1,4-galactosyltransferase (EC 2.4.1.38), which is also referred to as lactosylceramide synthase. This enzyme has been characterized from rat (Nomura et al. (1998) *J. Biol. Chem.* 273: 13570–7), and nucleotide sequences are available for the corresponding cDNA of chicken (GenBank Accession Nos. U19890 and U19889) and mouse (GenBank Accession No. L16840; Shaper et al. (1988) *J. Biol. Chem.* 263: 10420–10428).

In an alternative embodiment, the galactosylation is carried out using a β-galactosidase. The glycosphingoid precursor is contacted β-galactosidase and a compound having the formula Gal-X, where X is a leaving group attached to the 1-position of the galactose residue, under conditions suitable for transfer of the Gal residue from the Gal-X to the glucosylceramide. Suitable leaving groups include, for example, β-p-nibrophenyl, phenyl, methyl, methoxymethyl, and methoxyethyl ethers. Other activating groups are discussed in, for example, Nilsson et al. (1988) *Trends Biotechnol.* 6: 256, and citations therein. The use of galactosidases for adding a galactose to a saccharide is described in, for example, U.S. Pat. Nos. 5,403,726 and 5,374,541.

The glycosyltransferase used to add the next saccharide moiety (Step 3) will depend on the particular glycosphingolipid to be synthesized. In one embodiment, the invention provides methods of adding one or more sialic acid residues to a glycosylceramide to form a ganglioside. These methods make use of sialyltransferases, which comprise a family of glycosyltransferases that transfer sialic acid from the donor substrate CMP-sialic acid to acceptor oligosaccharide substrates. At least 15 different mammalian sialyltransferases have been documented, and the cDNAs of thirteen of these have been cloned to date (for the systematic nomenclature that is used herein, see, Tsuji et al. (1996) *Glycobiology* 6: v–xiv). In addition, two bacterial sialyltransferases have been recently reported (Yamamoto et al. (1996) *J. Biochem.* 120: 104–110; Gilbert et al. (1996) *J. Biol. Chem.* 271: 28271–28276).

An acceptor for the sialyltransferase will be present on the glycosylceramide to be modified by the methods of the present invention. Suitable acceptors, include, for example, galactosyl acceptors such as Galβ1,4GalNAc-, Galβ1, 3GalNAc-, lacto-N-tetraose-, Galβ1,3GlcNAc-, Galβ1, 4GlcNAc-, Galβ1,3Ara-, Galβ1,6GlcNAc-, and Galβ1, 4Glc-(lactose). Other acceptors known to those of skill in the art (see, e.g., Paulson et al. (1978) *J. Biol. Chem.* 253: 5617–5624). Typically, the acceptors form part of an oligosaccharide chain that is attached to a ceramide or other glycosphingoid moiety.

The particular sialyltransferase employed in the reactions will depend upon the ganglioside being synthesized. For the ganglioside GM3, for example, an α2,3 sialyltransferase is used, along with its acceptor CMP-sialic acid. A suitable enzyme for this reaction is described in Ishii (1997) *Glycoconj. J.* 14(supp. 1): S49.

Additional gangliosides can be synthesized by contacting α2,3-sialylated moieties with an α2,8-sialyltransferase, either after or simultaneously with the α2,3 sialyltransferase reaction. The α2,8-sialyltransferase catalyzes the addition of a sialic acid residue linked α2,8 to the α2-3-linked sialic acid. By this method, one can synthesize the gangliosides GD1a, GD1b, GT1a, GT1b, GT1c, and GQ1b, for example. The structures for these gangliosides, as well as those discussed above, are shown in Table 2. For example, to synthesize the ganglioside GD3, an α2,8 sialyltransferase is used, either simultaneously with or after the reaction with a α2,3 sialyltransferase. A suitable enzyme for this reaction is the ST8Sia I (GD3/GT3 synthase; EC 2.4.99.8; see, e.g., (human) Nara et al. (1994) *Proc. Natl. Acad. Sci USA* 91: 7952–7956; Haraguchi et al. (1994) *Proc. Natl. Acad. Sci. USA* 91:10455–10459; Sasaki et al. (1994) *J. Biol. Chem.* 269:15950–15956; Nakayama et al. (1996) *J. Biol. Chem.* 271:3684–3691) and mouse (Yoshida et al. (1995) *J. Biol Chem.* 270:14628–14633)), which links a sialic acid residue in an α2-8 linkage to a previously added α2-3-linked sialic acid. Another sialyltransferase, ST8GalNAcIII can be used to convert GM1 to GD1. The rat cDNA for this enzyme has been cloned and characterized (Sjoberg et al. (1996) *J. Biol. Chem.* 271:7450–7459; GenBank Accession No. L29554). Other α2-8-sialylatransferases include ST8SiaII, STX (Scheidegger et al. (1995) *J. Biol. Chem.* 270: 22685–22688) and ST8SiaIII, which utilizes Sia2,3Gal1,4GlcNAc as an acceptor, and thus is useful in methods for synthesizing neolactogangliosides (Yoshida et al. (1995) *J. Biol. Chem.* 270: 14628–14633). In a presently preferred embodiment, the two sialyltransferase reactions are carried out simultaneously.

For sialylation of the lacto- and neolacto-series of gangliosides, the sialyltransferase will be able to transfer sialic acid to the structures Galβ1,4GlcNAc- and Galβ1,4GlcNAc-, respectively. Suitable sialyltransferases include those that are summarized in Table 1.

TABLE 1

Sialyltransferases which use the Galβ1,4GlcNAc sequence as an acceptor substrate.

| Sialyltransferase | Source | Sequence(s) formed | Ref. |
| --- | --- | --- | --- |
| ST6Gal I | Mammalian | NeuAcα2,6Galβ1,4GlcNAc- | 1 |
| ST3Gal III | Mammalian | NeuAcα2,3Galβ1,4GlcNAc-<br>NeuAcα2,3Galβ1,3GlcNAc- | 1 |
| ST3Gal IV | Mammalian | NeuAcα2,3Galβ1,4GlcNAc-<br>NeuAcα2,3Galβ1,3GlcNAc- | 1 |
| ST6Gal II | photobacterium | NeuAcα2,6Galβ1,4GlcNAc- | 2 |
| ST3Gal V | N. meningitides<br>N. gonorrhoeae | NeuAcα2,3Galβ1,4GlcNAc- | 3 |

1) Goochee et al. (1991) Bio/Technology 9: 1347–1355
2) Yamamoto et al. (1996) J. Biochem. 120: 104–110
3) Gilbert et al. (1996) J. Biol. Chem. 271: 28271–28276

In addition to serving as a substrate for sialyltransferases, the lactosylceramide can also be utilized as the acceptor for a β1,4-galactosaminyltransferase (EC 2.4.1.92), which catalyzes the transfer of a GalNAc from UDP-GalNAc to the Gal moiety of the lactosylceramide. The nucleotide sequence for this enzyme is available for human (GenBank Accession No. M83651; Nagata et al. (1992) *J. Biol. Chem.* 267: 12082–12087), rat (GenBank Accession No. D17809;Hidari et al. (1994) *Biochem. J.* 301: 957–965), and mouse (GenBank Accession No. L25885; Sango et al. (1995) *Genomics* 27: 362–365), for example. Therefore, the enzyme is readily obtainable by recombinant methods.

To synthesize the ganglioside GM2 from the resulting GalNAcβ4Galβ4Glc-Cer moiety, an α2,3 sialyltransferase is employed, as discussed above. The ganglioside GD2 can be synthesized by the methods of the invention by use of an α2,8 sialyltransferase following, or simultaneously with, the reaction with the α2,3 sialyltransferase. Alternatively, an α2,6 sialyltransferase (ST6GalNAcI; EC 2.4.99.3) can be employed to add a sialic acid residue in an α2,6 linkage (Kurosawa et al. (1994) *J. Biol. Chem.* 269: 1402–1409).

The GalNAcβ4Galβ4Glc-Cer moiety can also be used as the acceptor for synthesis of additional glycosphingolipids. For example, the invention provides methods in which this compound is galactosylated using a β1,3 galactosyltransferase. A suitable galactosyltransferase for this application is described in, for example, Ghosh et al. (1995) *Glycoconj. J.* 12: 838–47.

To synthesize the gangliosides GM1a and GM1b from the resulting Galβ3GalNAcβ4Galβ4Glc-Cer moiety, the methods of the invention involve contacting the moiety with an α2,3 sialyltransferase. For example, the methods can use a ST3Gal III sialyltransferase (human: Sasaki et al. (1993) *J. Biol. Chem.* 268: 22782–22787; GenBank Accession No. x74570). The bacterial sialyltransferases are also suitable for this reaction (Table 1).

The invention also provides methods of adding sialic acid in an α2,6Gal linkage. For example, the use of ST6Gal I can catalyze the addition of a sialic acid in an α2,6Gal linkage. This enzyme is commercially available (Boehringer Mannheim Biochemicals, Indianapolis Ind.), and the cDNA has been cloned from several organisms, including rat (Weinstein et al. (1987) *J. Biol Chem.* 262: 17735–17743), human (Grundmann et al. (1990) *Nucl. Acids Res.* 18:667; Zettlmeisl et al. (1992) Patent EP 0475354; Stamenkovic et al. (1990) *J. Exp. Med.* 172:641–643, Bast et al. (1992) *J. Cell Biol.* 116:423–435), mouse (Hamamoto et al. (1993) *Bioorg. Med. Chem.* 1:141–145), and chicken (Kurosawa et al. (1994) *Eur. J. Biochem.* 219:375–381). Other gangliosides can be synthesized using ST6GalNAcII, which adds an α2,6-linked sialic acid to the Galβ3GalNAc-moiety (chicken, Kurosawa et al. (1994) *J. Biol. Chem.* 269: 19048–19053, GenBank Accession No. x77775).

Figure 2:
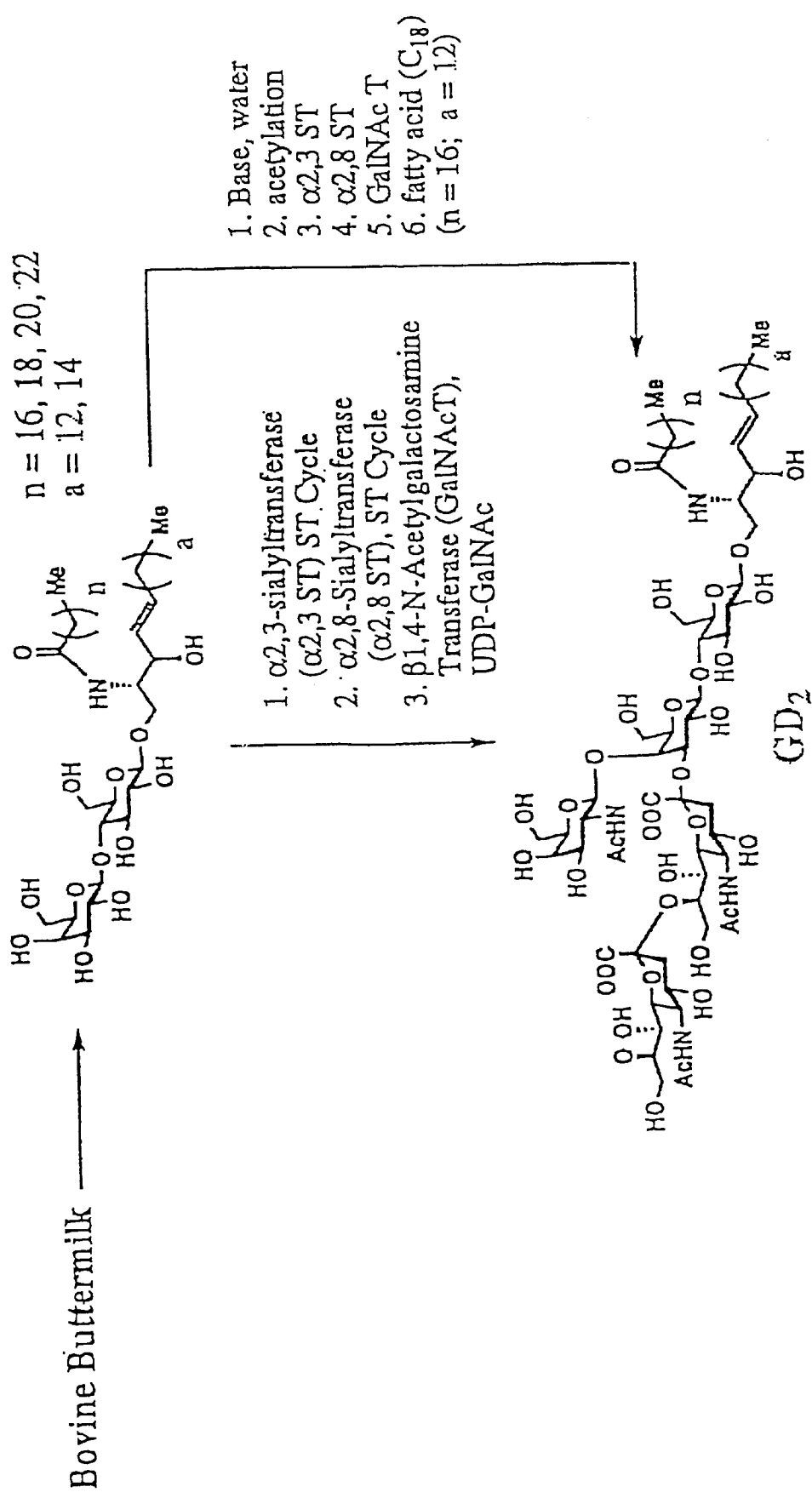
FIG. 2 shows a schematic diagram of two methods for synthesizing the ganglioside GD$_2$ from lactosylceramide obtained from bovine buttermilk.

The sialyltransferases and other glycosyltransferases can be used either alone or in conjunction with additional enzymes. For example, FIG. 2 shows a schematic diagram of two pathways for synthesis of the ganglioside GD$_2$ starting from lactosylceramide. Each pathway involves the use of two different sialyltransferases (an α2,3ST and an α2,8ST), as well as a GalNAc transferase. In the preferred pathway, the fatty acid is removed from the lactosylceramide by treatment with base (Step 1). Acetylation is then performed (Step 2), after which a sialic acid is attached to the galactose residue in an α2,3 linkage by an α2,3 sialyltransferase (Step 3). The sialylation steps are performed, preferably in the presence of an organic solvent as described herein, thereby driving the reaction nearly to completion. A GalNAc residue is then added to the galactose in a β1,4 linkage using a GalNAc transferase (Step 5). Finally, a fatty acid is added, e.g., by reaction with steroyl chloride, to complete the ganglioside (Step 6).

One of skill in the art, using the guidance provided herein, can choose additional glycosyltransferases, alone or in combination, that can catalyze the synthesis of other glycosphingolipids of interest. For example, to synthesize a lacto- or neolacto-glycosphingolipid, one would replace the β1,4 galactosaminyltransferase in Step 3 above with a β1,3GlcNAc transferase. Contacting the product of this reaction with a β1,3 galactosyltransferase (lacto) or aβ1,4 galactosyltransferase (neolacto) will then provide the acceptor for the appropriate sialyltransferase or sialyltransferases to synthesize a ganglioside, as desired. An example of a sialyltransferase that is useful in these methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al. (1992) J. Biol. Chem., 267: 21011–21019; Van den Eijnden et al. (1991) J. Biol. Chem., 256: 3159). The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) J. Biol. Chem., 257: 13845); the human cDNA (Sasaki et al. (1993) J. Biol. Chem. 268:22782–22787; Kitagawa & Paulson (1994) J. Biol. Chem. 269:1394–1401) and genomic (Kitagawa et al. (1996) J. Biol Chem. 271:931–938) DNA sequences are known, facilitating production of this enzyme by recombinant expression. In one embodiment, the methods of the invention use a rat ST3Gal III.

Similarly, one can synthesize the globo- and isoglobo-glycosphingolipids by replacing the β1,4-galactosaminyltransferase in Step 3 above with an α1,4- (globo) or an α1,3-galactosyltransferase (isoglobo). The products of these reactions are subjected to β1,3GalNAc transferase-catalyzed addition of a GalNAc residue to the nonreducing Gal residue. Again, treatment of the product with one or more sialyltransferases will yield a desired ganglioside.

Gangliosides and other glycosphingolipids sometimes include other sugars in addition to those described above. For example, fucose residues are sometimes present. Accordingly, the invention provides methods of synthesizing these fucosylated glycosphingolipids. These methods involve the use of a fucosyltransferase to catalyze the transfer of a fucose residue from an activated nucleotide sugar (GDP-fucose) to an appropriate acceptor. For example, one can contact a GM1a ganglioside with an α1,2-fucosyltransferase to obtain a ganglioside having the structure Fucα2Galβ3GalNAcβ4 (Siaα3)Galβ4Glc-Cer (Wiegandt (1973) H.-S. Zschr. Physiol. Chem. 354: 1049–1056).

The methods of the invention are useful for producing any of a large number of gangliosides and related structures. Many gangliosides of interest are described in Oettgen, H. F., ed., Gangliosides and Cancer, VCH, Germany, 1989, pp. 10–15, and references cited therein. Gangliosides of particular interest include, for example, those found in the brain as well as other sources which are listed in Table 2.

TABLE 2

Ganglioside Formulas and Abbreviations

| Structure | Abbreviation |
|---|---|
| Neu5Ac3Gal4GlcCer | GM3 |
| GalNAc4(Neu5Ac3)Gal4GlcCer | GM2 |
| Gal3GalNAc4(Neu5Ac3)Gal4GlcCer | GM1a |

TABLE 2-continued

Ganglioside Formulas and Abbreviations

| Structure | Abbreviation |
|---|---|
| Neu5Ac3Gal3GalNAc4Gal4GlcCer | GM1b |
| Neu5Ac8Neu5Ac3Gal4GlcCer | GD3 |
| GalNAc4(Neu5Ac8Neu5Ac3)Gal4GlcCer | GD2 |
| Neu5Ac3Gal3GalNAc4(Neu5Ac3)Gal4GlcCer | GD1a |
| Neu5Ac3Gal3(Neu5Ac6)GalNAc4Gal4GlcCer | GD1α |
| Gal3GalNAc4(Neu5Ac8Neu5Ac3)Gal4GlcCer | GD1b |
| Neu5Ac8Neu5Ac3Gal3GalNAc4(Neu5Ac3)Gal4GlcCer | GT1a |
| Neu5Ac3Gal3GalNAc4(Neu5Ac8Neu5Ac3)Gal4GlcCer | GT1b |
| Gal3GalNAc4(Neu5Ac8Neu5Ac8Neu5Ac3)Gal4GlcCer | GT1c |
| Neu5Ac8Neu5Ac3Gal3GalNAc4(Neu5Ac8Neu5c3)Gal4GlcCer | GQ1b |

Nomenclature of Glycolipids, IUPAC-IUB Joint Commission on Biochemical Nomenclature (Recommendations 1997); Pure Appl. Chem. (1997) 69: 2475–2487; Eur. J. Biochem (1998) 257: 293–298) (www.chem.qmw.ac.uk/iupac/misc/glylp.html).

In some embodiments, the invention provides methods for in vitro sialylation of saccharide groups present on a glycosylceramide, wherein the methods first involve modifying the glycosylceramide to create a suitable acceptor. A preferred method for synthesizing an acceptor involves use of a galactosyltransferase. The steps for these methods include:

(a) galactosylating a compound of the formula Glcβ-OR with a galactosyltransferase in the presence of a UDP-galactose under conditions sufficient to form the compound: Galβ(1-4)Glcβ-OR; and (b) sialylating the compound formed in (a) with a sialyltransferase in the presence of a CMP derivative of a sialic acid using a α(2,3)sialyltransferase under conditions in which sialic acid is transferred to the non-reducing sugar to form the compound NeuAcα(2-3)Galβ(1-4)Glc-β-OR. In this formula, R is a ceramide or sphingoid. In some embodiments, this product is contacted with an α2,8-sialyltransferase under conditions in which a sialic acid residue is transferred to the α2,3-linked sialic acid to form the compound NeuAcα(2-8)NeuAcα(2-3)Galβ(1-4)Glc-β-OR.

In additional embodiments, the Galβ(1-4)Glcβ-OR compound formed in step (a) is further modified, either before or after the sialylation step (b). For example, the methods can involve the additional steps of:

(c) adding a GalNAc residue to Galβ(1-4)Glcβ-OR by contacting the compound with a β1,4-galactosaminyltransferase in the presence of UDP-GalNAc under conditions in which GalNAc is transferred to the non-reducing end of the oligosaccharide to form GalNAcβ (1-4) Galβ(1-4)Glcβ-OR; and (d) adding a Gal residue to GalNAcβ(1-4) Galβ(1-4) Glcβ-OR by contacting the compound formed in step (c) with a β1-3-galactosyltransferase in the presence of UDP-Gal, under conditions in which Gal is transferred to the non-reducing end of the oligosaccharide to form Galβ(1-3)GalNAcβ(1-4)Galβ(1-4)Glcβ-OR.

Further embodiments of the invention involve synthesis of gangliosides by:

(e) contacting the product of step (d) with one or more sialyltransferases as described in step (b), under conditions in which sialic acid is transferred to either or both of the Gal residues. This reaction can involve, for example, an α2-3-sialyltransferase alone, or an α2-3-sialyltransferase and an α2,8-sialyltransferase.

The sphingoids that can be used as starting materials in the methods of the invention include, but are not limited to, those that have the formula I:

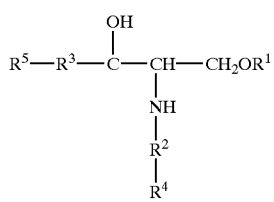

wherein
$R^1$ is selected from the group consisting of H, Glcβ1-, Galβ1-, and lactoseβ1-;
$R^2$ is selected from the group consisting of $CH_2$ and

$R^3$ is selected from the group consisting of H, $CH_3$, $CH_2CH_3$,

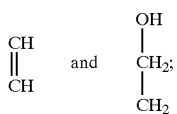

$R^4$ is selected from the group consisting of:
(i) $C_2-C_{36}$ saturated, unsaturated, or polyunsaturated alkyl;
(ii) α-hydroxy-$C_2-C_{36}$ alkyl;
(iii) ω-hydroxy-$C_2-C_{36}$ alkyl;
(iv) α, ω-dihydroxy-$C_2-C_{36}$ alkyl; and
(v) an alkanoyl group having the formula

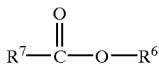

in which $R^6$ is either a divalent $C_2-C_{36}$ alkyl or a divalent α-hydroxy-$C_2-C_{36}$ alkyl, and $R^7$ is either a monovalent $C_2-C_{36}$ alkyl or a monovalent α-hydroxy-$C_2-C_{36}$ alkyl; and
$R^5$ is selected from the group consisting of a saturated, unsaturated, or polyunsaturated $C_2-C_{37}$ alkyl group.

In some embodiments, the sphingoids comprise the formula II:

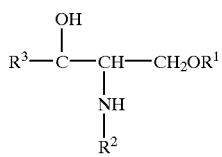

wherein
$R^1$ is selected from the group consisting of H, Glcβ1-, Galβ1-, lactoseβ1-, and an oligosaccharide;

$R^2$ is selected from the group consisting of H, a saturated or unsaturated $C_2-C_{26}$ alkyl group, and a protecting group; and
$R^3$ is a saturated, unsaturated, or polyunsaturated $C_2-C_{37}$ alkyl group, or a protecting group.

Sphingoids of particular interest include, for example, sphingosines, phytosphingosines, sphinganines, and ceramides. The sphingoids can be naturally occurring or can be produced synthetically or semisynthetically. An example of a semisynthetically produced ganglioside derivative that one can produce using the methods of the invention is the N-dichloroacetylsphingosine compounds described in Kharlamov et al. (1994) *Proc. Nat'l. Acad. Sci. USA* 91: 6303–6307 (e.g., LIGA20) and Schneider et al. (1994) *Neurology* 44: 748, in which $R^2$ in the above formula II includes the lipid moiety 2-dichloroacetylamide. In some embodiments, the dicloroacetylsphingosine compounds have $R^3$ in formula II as being 4-trans-octadecene.

Thus, the invention provides methods of synthesizing glycosphingoids having the formula III:

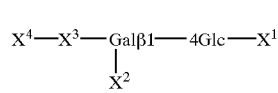

wherein
$X^1$ is a sphingoid, such as a ceramide or a sphingosine, for example;
$X^2$ and $X^4$ are each independently selected from the group consisting of -H, Siaα2-3-, Siaα2-6-, Siaα2-8-Siaα2-3-, and Fucα1-2-;
$X^3$ is optional and, if present, is selected from the group consisting of GalNAcβ1-4-, Galβ1-3GalNAcβ1-4-, Fucα1-2Galβ1-3GalNAcβ1-4-, Galβ1-3GlcNAcβ1-3-, Galβ1-4GlcNAcβ1-3-, GalNAcβ1-3Galα1-4-, and GalNAcβ1-3Galα1-3-.

The present invention also provides methods of synthesizing analogs of gangliosides and other glycosphingolipids. For example, one can use glycosyltransferases as described above, except that an analog of a sugar is attached to the activated nucleotide which serves as the saccharide donor. The analog is chosen so that the analog-nucleotide is still capable of serving as a donor for the glycosyltransferase of interest. Examples of suitable analogs for synthesizing gangliosides are described in, for example, U.S. Pat. No. 5,352,670.

B. Removal of Fatty Acids

In some embodiments, the methods of the invention involve removal of a fatty acid moiety from a glycoceramide or sphingoid prior to reaction with the glycosyltransferase. Methods of removing a fatty acid moiety from a glycosphingolipid are known to those of skill in the art. Standard carbohydrate and glycosphingolipid chemistry methodology can be employed, such as that described in, for example, Paulson et al. (1985) *Carbohydrate Res.* 137: 39–62; Beith-Halahmi et al. (1967) *Carbohydrate Res.* 5: 25–30; Alais and Veyrieries (1990) *Carbohydrate Res.* 207: 11–31; Grudler and Schmidt, (1985) *Carbohydrate Res.* 135: 203–218; Ponpipom et al. (1978) *Tetrahedron Lett.* 1717–1720; Murase et al. (1989) *Carbohydrate Res.* 188: 71–80; Kameyama et al. (1989) *Carbohydrate Res.* 193: c1–c5; Hasegawa et al. (1991) *J. Carbohydrate Chem.* 10: 439–459;

Schwarzmann and Sandhoff (1987) *Meth. Enzymol.* 138: 319–341; Guadino and Paulson (1994) *J. Am. Chem. Soc.* 116: 1149–1150 (including supplemental material, which is also incorporated herein by reference). For example, hydrolysis of the fatty acid moiety can be effected by base hydrolysis.

Once the glycosylation reactions are completed, one can attach the same or a different fatty acid to the product of the glycosylation reactions. Methods for coupling a fatty acid are known to those of skill in the art.

C. Use of Organic Solvents

In some embodiments, the glycosyltransferase reactions are carried out in the presence of an organic solvent. In presently preferred embodiments, the fatty acid moiety is first hydrolyzed as described above. The enzymatic catalyses can be carried out in the presence of an organic solvent, such as, for example, methanol, ethanol, dimethylsulfoxide, isopropanol, tetrahydrofuran, chloroform, and the like, either singly or in combination. The proportion of the organic solvent in the reaction mixture is typically at least about 3%, more preferably at least about 5%, and most preferably at least about 8%. The reaction mixture typically contains about 25% or less of organic solvent, more preferably about 20% or less, and most preferably about 10% or less organic solvent. In a presently preferred embodiment, the reaction mixture contains about 8–10% methanol.

The use of an organic solvent in the reaction mixture provides several advantages over previously described enzymatic synthesis methods of glycosylceramides. A previously known method for synthesis of the neolacto series ganglioside 6'-nLM$_1$ was completed with less than 5% yield based on sialic acid (Hasegawa et al. (1991) *J. Carbohydrate Chem.* 10: 439–459). A subsequently reported method which involved removal of the fatty acid in conjunction with the presence of a detergent in the reaction mixture obtained a yield of only 30–40% (Guadino and Paulson, supra.). The use of an organic solvent as provided by the present invention not only results in a much higher yield than was obtainable previously, it also eliminates the need for a detergent to increase accessibility to the glycosyl moiety of the glycosylceramide. This facilitates purification of the resulting ganglioside. However, detergents can also be used in the methods of the invention.

D. Glycosyltransferase Reaction Conditions

The glycosylation steps in the methods of the invention are preferably carried out enzymatically. In a preferred embodiment, a plurality of enzymatic steps are carried out in a single reaction mixture that contains two or more different glycosyltransferases. For example, one can conduct a galactosylating and a sialylating step simultaneously by including both sialyltransferase and galactosyltransferase in the reaction mixture. In this embodiment, the enzymes and substrates can be combined in an initial reaction mixture, or preferably the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated. Moreover, cleanup and disposal of extra solvents and by-products is reduced.

Enzyme amounts or concentrations are expressed in activity Units, which is a measure of the initial rate of catalysis. One activity Unit catalyzes the formation of 1 μmol of product per minute at a given temperature (typically 37° C.) and pH value (typically 7.5). Thus, 10 Units of an enzyme is a catalytic amount of that enzyme where 10 μmols of substrate are converted to 10 μmol of product in one minute at a temperature of 37° C. and a pH value of 7.5. The enzymes can be utilized free in solution or can be bound to a support such as a polymer. The reaction mixture is thus substantially homogeneous at the beginning, although some precipitate can form during the reaction.

The glycosylation reactions include, in addition to the appropriate glycosyltransferase and acceptor, an activated nucleotide sugar that acts as a sugar donor for the glycosyltransferase. The reactions can also include other ingredients that facilitate glycosyltransferase activity. These ingredients can include a divalent cation (e.g., $Mg^{+2}$ or $Mn^{+2}$), materials necessary for ATP regeneration, phosphate ions, and organic solvents. The concentrations or amounts of the various reactants used in the processes depend upon numerous factors including reaction conditions such as temperature and pH value, and the choice and amount of acceptor saccharides to be glycosylated. The reaction medium may also comprise solubilizing detergents (e.g., Triton or SDS) and organic solvents such as methanol or ethanol, if necessary.

In optimized reactions, the above ingredients can be combined by admixture in an aqueous reaction medium (solution) which has a pH value of about 6 to about 8.5. The medium is devoid of chelators that bind enzyme cofactors such as $Mg^{+2}$ or $Mn^{+2}$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8.5, preferably about 7.2 to 7.8, by the addition of base. A suitable base is NaOH, preferably 6 M NaOH.

The temperature at which an above process is carried out can range from just above freezing to the temperature at which the most sensitive enzyme denatures. That temperature range is preferably about zero degrees C. to about 110° C., and more preferably at about 20° C. to about 30° C., or higher for a thermophilic organism.

The reaction mixture so formed is maintained for a period of time sufficient for the glycosyltransferase(s) to glycosylate a high percentage of the acceptors. Some of the product can often be detected after a few hours, with recoverable amounts usually being obtained within 24 hours. For commercial-scale preparations, the reaction will often be allowed to proceed for about 8–240 hours, with a time of between about 24 and 48 hours more typical.

In some presently preferred embodiments, the glycosylation steps are carried out using a half-cycle or full cycle in which one or more reaction components are regenerated. Glycosyltransferase cycles and half-cycles are described in U.S. Pat. No. 5,728,554. For example, the galactosylating step can be carried out as part of a galactosyltransferase cycle and the sialylating step is preferably carried out as part of a sialyltransferase cycle. Preferred conditions and descriptions of other species and enzymes in each of these, and other, cycles have been described. See, e.g., commonly assigned U.S. Provisional Application No. 60/071,076, filed Jan. 15, 1998 and U.S. patent application Ser. No. 08/628,543, filed Apr. 10, 1996.

As an example, the sialylation of the glycosylceramide can be accomplished using a sialyltransferase cycle, which includes a CMP-sialic acid recycling system that utilizes CMP-sialic acid synthetase. CMP-sialic acid is relatively expensive, so in situ synthesis of this sialic acid donor moiety enhances the economic advantages provided by the claimed methods. Sialyltransferase cycles are described, for example, in U.S. Pat. No. 5,374,541. The CMP-sialic acid regenerating system used in this embodiment comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP.

The regenerating system also employs CMP-sialic acid synthetase, which transfers sialic acid to CMP. CMP-sialic acid synthetase can be isolated and purified from cells and tissues containing the synthetase enzyme by procedures well known in the art. See, for example, Gross et al. (1987) Eur. J. Biochem., 168: 595; Vijay et al. (1975) J. Biol. Chem. 250: 164; Zapata et al. (1989) J. Biol. Chem. 264: 14769; and Higa et al. (1985) J. Biol. Chem. 260: 8838. The gene for this enzyme has also been sequenced. See, Vann et al. (1987) J. Biol. Chem., 262:17556. Overexpression of the gene has been reported for use in a gram scale synthesis of CMP-NeuAc. See, Shames et al. (1991) Glycobiology, 1:187. This enzyme is also commercially available.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated galactosyl glycoside. Preferred phosphate donors are phosphoenolpyruvate (PEP) and acetyl phosphate. A particularly preferred phosphate donor is PEP.

The selection of a particular kinase for use in a sialic acid cycle depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (e.g. free Neu5Ac and PEP) is consumed.

In the sialylation cycle, CMP is converted to CDP by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the galactosyl glycoside, the released CMP re-enters the regenerating system to reform CDP, CTP and CMP-sialic acid. The formed PPi is scavenged as discussed below, and forms inorganic phosphate (Pi) as a byproduct. Pyruvate is also a byproduct.

The byproduct pyruvate can also be made use of in another reaction in which N-acetylmannosamine (ManNAc) and pyruvate are reacted in the presence of NeuAc aldolase (EC 4.1.3.3) to form sialic acid. Thus, the sialic acid can be replaced by ManNAc and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase coupled with inorganic pyrophosphatase (PPase)-catalyzed decomposition of the released inorganic pyrophosphate. This enzymatic synthesis of sialic acid and its 9-substituted derivatives and the use of a resulting sialic acid in a different sialylating reaction scheme is disclosed in International application WO 92/16640, published on Oct. 1, 1992.

As used herein, the term "pyrophosphate scavenger" refers to substances that serve to remove inorganic pyrophosphate from a reaction mixture of the present invention. Inorganic pyrophosphate (PPi) is a byproduct of the preparation of CMP-Neu5Ac. Produced PPi can feed back to inhibit other enzymes such that glycosylation is reduced. However, PPi can be degraded enzymatically or by physical means such as sequestration by a PPi binding substance. Preferably, PPi is removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.), and that or a similar enzyme serves as the pyrophosphate scavenger. One method of removing PPi or Pi from the reaction mixture is to maintain divalent metal cation concentration in the medium. In particular, the cations and the inorganic phosphate produced form a complex of very low solubility. By supplementing the cations which are lost by precipitation with pyrophosphate, the rate of reaction can be maintained and the reactions can be taken to completion (ie., 100% conversion). Supplementing can be carried out continuously (e.g., by automation) or discontinuously. When cation concentration is maintained in this way, the transferase reaction cycle can be driven to completion.

For glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants. Preferably, the concentrations of activating nucleotides, phosphate donor, the donor sugar and enzymes are selected such that glycosylation proceeds until the acceptor is consumed, thus completely sialylating the saccharide groups present on the glycoprotein.

In some presently preferred embodiments, the glycosylation reactions are conducted by contacting the acceptor with a cell that contains: a) an enzymatic system for producing a nucleotide sugar, and b) a recombinant glycosyltransferase which catalyzes the transfer of a sugar from the nucleotide sugar to the acceptor to produce the desired glycosphingoid. The cells are generally permeabilized and added to the reaction mixture. For reactions that require multiple glycosyltransferase steps, one can use cells that contain more than one recombinant glycosyltransferase and produce the corresponding nucleotide sugar for both glycosyltransferases. Mixtures of cell types that each contain one or more glycosyltransferase can be used, or multiple glycosyltransferase systems can be present in one cell type. Suitable methods are described in, for example, commonly assigned patent applications, each entitled "Low Cost Manufacture Of Oligosaccharides", filed on Nov. 18, 1998 as Ser. No. 60/109,032 and on Nov. 19, 1998 as Ser. No. 60/109,096.

The products produced by the above processes can be used without purification. However, it is usually preferred to recover the product. To purify glycolipids and gangliosides, standard methods for glycolipid preparation can be used (see, e.g., Ledeen et al. (1973) *J. Neurochem.* 21:829). For example, glycolipids can be extracted from a reaction mixture by chloroform/methanol 2:1 and isopropyl alcohol/hexane/water 55:25:20 as described by Kannagi et al. (1982) *J. Biol. Chem.* 257: 14865. The resulting extracts are partitioned by a chloroform/methanol/water (3:2:1) Folch partition. The resulting upper phase of the extraction contains gangliosides and the lower phase contains glycolipids. The upper phase containing gangliosides (glycosphingolipids that contain at least one sialic acid moiety) are isolated and separated into neutral and acidic fractions using DEAE-Sephadex chromatography as described in detail by Ledeen and Yu, *Methods Enzymol.* 83: 139 (1982). The resulting gangliosides are pooled, lyophilized, and dissolved in chloroform/methanol (2:1). The lower phase of the Folch partition contains glycolipids. These are isolated and separated on preparative thin-layer chromatography using chloroform/methanol/water (60:35:8) as the solvent system as described by Symington.

Other standard, well known techniques for recovery of glycosylated saccharides are suitable, including such as thin or thick layer chromatography and ion exchange chromatography. A preferred method of purification involves membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins. Nanofiltration or reverse osmosis can then be used to remove salts and/or purify the soluble oligosaccharide products (see, e.g., U.S. patent application Ser. No. 08/947,775, filed Oct. 9, 1997). Nanofilter membranes are a class of reverse osmosis membranes which pass monovalent salts but retain polyvalent salts and uncharged solutes larger than about 100 to about 700 Daltons, depending upon the membrane used. Thus, in a typical application, saccharides prepared by the methods of the present invention will be retained in the membrane and contaminating salts will pass through.

To identify those gangliosides and glycolipids which contain a desired oligosaccharide, immunochemical glycolipid analysis can be performed according to the procedure of Magnani et al. (1980) *Anal. Biochem.* 109: 399. Briefly, the ganglioside pool described above is chromatographed by thin layer chromatography. The thin layer plate is then incubated with $^{125}$I labeled antibody that binds specifically to the oligosaccharide of interest (e.g., FH6, which binds specifically to SLX). Following incubation with the labeled antibody, the plate is exposed to radiographic detection film and developed. Black spots on the X-ray film correspond to gangliosides that bind to the monoclonal antibody, and those gangliosides are recovered by scraping the corresponding areas of the silica plate and eluting the gangliosides with chloroform/methanol/water. Glycolipids are also dried and resuspended in chloroform and developed in a similar thin layer system and probed with the radiolabeled antibody.

Other methods by which one can analyze the oligosaccharides produced using the methods of the invention are known to those of skill in the art. For example, the carbohydrate units can be released from the glycosphingoids or glycosylceramides by alkaline β-elimination, for example, and separated from the ceramide or sphingoid moieties by gel filtration. The resulting oligosaccharides are then separated from each other using a combination of gel filtration, HPLC, thin layer chromatography, and ion exchange chromatography, and can be fully analyzed. Complete structural analysis of the purified oligosaccharide units requires the determination of the monosaccharide units, their ring form, configuration (D or L), anomeric linkage (α or β), the positions of the linkages between the sugars and their sequence. In addition, the position of any substituent groups are established. Methylation analysis is used to determine the positions of the glycosidic linkages between the monosaccharides. The anomeric configuration of the sugar residues can be addressed using 500-MHz$^1$H NMR spectroscopy. The conditions and methods used to perform a complete structural carbohydrate analysis are described generally in Beeley, *Laboratory Techniques in Biochemistry and Molecular Biology,* eds. Burdon and Knippenberg, Elsevier, Amsterdam (1985), Hounsell, "Glycoanalysis Protocols", *Meth. Mol. Biol.* Vol. 76, 1998, and El Rassi, *Carbohydrate Analysis: High Performance Liquid Chromatography and Capillary Electrophoresis,* Elsevier Science Ltd, Vol. 58 (1994).

Additional techniques to fully characterize the sugars of an oligosaccharide include FAB-MS (fast atom bombardment-mass spectrometry), HPAE (high pH anion exchange chromatography) and $^1$H-NMR. These techniques are complementary. Recent examples of how these techniques are used to fully characterize the structure of an oligosaccharide can be found in the analysis by Spellman et al., (1989) *J. Biol. Chem.* 264: 14100, and Stanley et al. (1988) *J. Biol. Chem.* 263: 11374. Other methods include positive ion fast atom bombardment mass spectroscopy (FAB-MS) and methylation analysis by gas chromatography-electron impact mass spectroscopy (GC/EI-MS) (see, EPO Application No. 89305153.2).

E. Uses for Gangliosides and Glycosphingoids

The gangliosides other compounds that are made using the methods of the invention can be used in a variety of applications, e.g., as antigens, diagnostic reagents, or as therapeutics. For example, gangliosides have been reported to be useful for treating spinal cord and other nervous system injuries (see, e.g., Skaper et al. (1989) *Mol. Neurobiol.* 3: 173; Samson (1990) *Drug Devel. Rev.* 19: 209–224), stroke, subarachnoid hemorrhage, cognition defects (Kharlamov et al. (1994) *Proc. Nat'l. Acad. Sci. USA* 91: 6303–6307), Parkinson's disease (Schneider (1998) *Ann. N.Y Acad. Sci.* 845: 363–73), glutamate neurotoxicity (Costa et al. (1994) In *Cirrhosis, Hyperammonemia, and Hepatic Encephalopathy,* Grisolin and Felipo, Eds., Plenum Press, NY, 1994, p. 129), and other conditions. For review, see, e.g., Nobile-Orazio et al. (1994) *Drugs* 47: 576–585). Gangliosides are involved in the local immunosuppression that is often associated with tumors (Rodden et al. (1991) *J. Neurosurg.* 74: 606–619), so agents that block or disrupt these gangliosides are useful in reducing the inaccessibility of tumors to the immune system. The immunosuppressive effect of gangliosides is useful for, e.g., suppressing rejection of transplanted organs.

Thus, the present invention also provides pharmaceutical compositions which can be used in treating a variety of conditions. The pharmaceutical compositions include the gangliosides or glycosphingoids synthesized using the methods of the invention, along with a pharmaceutically acceptable carrier. Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985). For a brief review of methods for drug delivery, see, e.g., Langer, *Science* 249:1527–1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously.

Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the gangliosides and other glycosphingoids made using the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028. The targeting of liposomes using a variety of targeting agents (e.g., the oligosaccharide moieties of the gangliosides of the invention) is well known in the art (see, e.g., U.S. Pat. Nos. 4,957,773 and 4,603,044).

The compositions containing the gangliosides and other glycosphingoids can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this use will depend on the severity of the disease and the weight and general state of the patient, but generally range from about 0.5 mg to about 40 g of oligosaccharide per day for a 70 kg patient, with dosages of from about 5 mg to about 20 g of the compounds per day being more commonly used.

Single or multiple administrations of the compositions can be carried out with dose levels and pattern being selected by the treating physician. In any event, the pharmaceutical formulations should provide a quantity of the oligosaccharides of this invention sufficient to effectively treat the patient.

The gangliosides and other glycosphingoids may also find use as diagnostic reagents. Diagnostic reagents that contain gangliosides made by the methods of the invention, or moieties that bind to the specific gangliosides (e.g., lectins and antibodies), are useful in diagnosing several conditions, including, for example, Fabry disease (-Gal--Gal--GalCer), Farber disease (ceramides; N-acylsphingosines), Gaucher disease (glucocerebroside), GM1 gangliosidosis (GM1 ganglioside), metachromatic leukodystrophy (sulfatide; cerebroside sulfate), Sandhoff disease (GM2 ganglioside), Tay-Sachs disease (GM2 ganglioside). For this use, the compounds can be labeled with appropriate labels, including radioisotopes such as, for example, $^{125}$I, $^{14}$C, or tritium.

The gangliosides and other glycosphingoids made using the methods of the invention can be used as an immunogen for the production of monoclonal or polyclonal antibodies specifically reactive with the compounds. The multitude of techniques available to those skilled in the art for production and manipulation of various immunoglobulin molecules can be used in the present invention. Antibodies may be produced by a variety of means well known to those of skill in the art. If desired, the production of antibodies can be enhanced by coupling the ganglioside or other glycosphingolipid to an immunogenic protein (e.g.,KLH) prior to administering the compound to the test animal (see, PCT application PCT/US94/00757, Publ. No. WO 94/16731). Uses for antibodies against gangliosides and other glycosphingolipids include cancer diagnosis and are described in, for example, U.S. Pat. No. 4,887,931.

The production of non-human monoclonal antibodies, e.g., murine, lagomorpha, equine, etc., is well known and may be accomplished by, for example, immunizing the animal with a preparation containing the oligosaccharide of the invention. Antibody-producing cells obtained from the immunized animals are immortalized and screened, or screened first for the production of the desired antibody and then immortalized. For a discussion of general procedures of monoclonal antibody production, see, Harlow and Lane, *Antibodies, A Laboratory Manual* Cold Spring Harbor Publications, N.Y. (1988).

The following Examples are offered to illustrate, but not to limit, the present invention.

EXAMPLE 1

Sialylation of Lyso-lactosyl Ceramide

This Example describes the reaction conditions for sialylation of lyso-lactosyl ceramide. Lactosylceramide was obtained from bovine buttermilk and the fatty acid moiety removed by base hydrolysis to form lyso-lactosyl ceramide. A mixture of the lyso-lactosyl ceramide (1.0 mg, 1.6 μmol) and CMP-sialic acid (2.46 mg, 65% purity, 2.40 μmol in HEPES buffer (200 mM, containing 8% MeOH, pH 7.5, 50 μL) was sonicated for twenty minutes. α2,3 sialyltransferase (10 μL, 5 U/mL, 50 mU) was then added followed by alkaline phosphatase (1 μL, $1.0 \times 10^5$ U/mL, 100 U). The reaction mixture was kept at room temperature. After one day, a further portion of α2,3 sialyltransferase (10 μL, 5 U/mnL, 50 mU) was added. After four more days, an additional portion of α2,3 sialyltransferase (10 μL, 5 U/mL, 50 mU) was added. After an additional one day at room temperature, thin layer chromatography indicated that the reaction was nearly complete.

EXAMPLE 2

Synthesis of GM2 from Lactosylceramide Obtained From Bovine Buttermilk

A schematic diagram of showing two pathways for synthesis of the ganglioside $GM_2$ from lactosylceramide obtained from bovine buttermilk is shown in FIG. 1. In the pathway shown at left, the fatty acid is not removed from the lactosylceramide prior to sialylation, and the reaction is not carried out in the presence of an organic solvent. The reaction at right, in contrast, is carried out in the presence of an organic solvent, and with removal of the fatty acid.

First, the fatty acid is hydrolyzed from the lactosylceramide by treatment with a base and water (Step 1). A sialic acid residue is then added by enzymatic transfer to the galactose residue using an α2,3 sialyltransferase, preferably an ST3GalIV (Step 2). This reaction can be carried out in the presence of an organic solvent. A GaNAc residue is then attached to the galactose in a β1,4 linkage using a GalNAc transferase (Step 3); this step may or may not be carried out in the presence of an organic solvent. Finally, the fatty acid moiety is reattached to the sphingosine to obtain the desired $GM_2$ ganglioside. The reaction typically proceeds nearly to completion due to the presence of an organic solvent during the sialylation.

EXAMPLE 3

Synthesis of Gangliosides from Plant Glucosyl Ceramide

Figure 3:
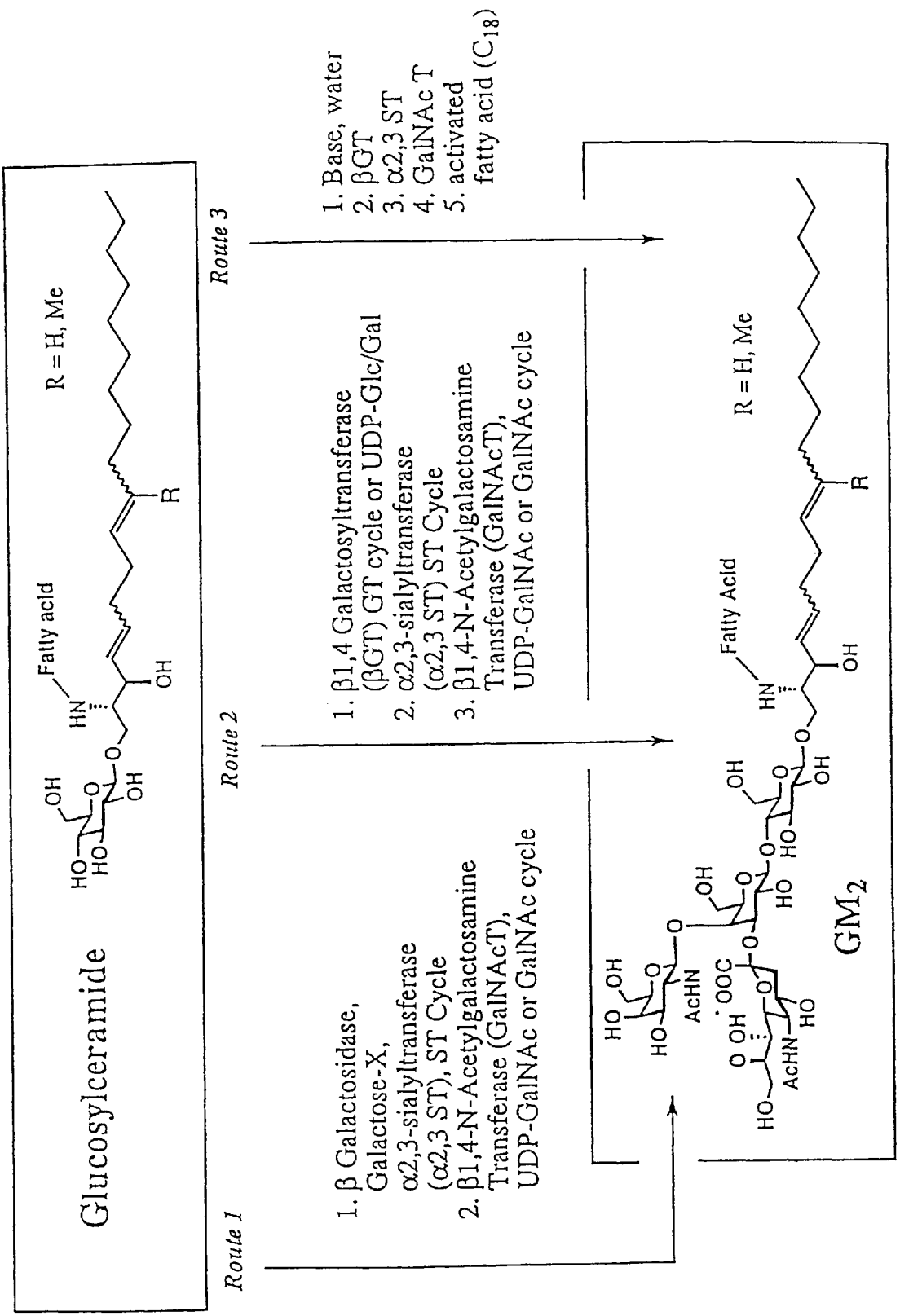
FIG. 3 shows three routes for synthesizing a GM2 ganglioside using a plant glucosylceramide as the starting material.

This Example describes three alternative procedures for the synthesis of the GM2 ganglioside using plant glucosylceramide as the precursor (FIG. 3). In Route 1, β1,4-galactosidase is used to catalyze the transfer of a Gal residue to the glycosylceramide. Simultaneously, an α2,3-sialyltranasferase is used in a sialyltransferase cycle to link a sialic acid residue to the Gal. Next, a β1,4-GalNAc transferase is added to the reaction mixture, either with UDP-GalNAc or as part of a GalNAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or UDP-Glc/Gal as the acceptor sugar. Sialylation and addition of GalNAc are carried out as described above to obtain GM2.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. The fatty acid can be the same as that originally found on the plant glucosylceramide, or can be different. In the example shown in FIG. 3, an activated $C_{18}$ fatty acid is used, resulting in the synthesis of GM2. Greater efficiency is generally observed when the fatty acid is removed prior to the glycosylation reactions.

EXAMPLE 4

Synthesis of Ganglioside GM2 from Glycosylceramide

Figure 4:
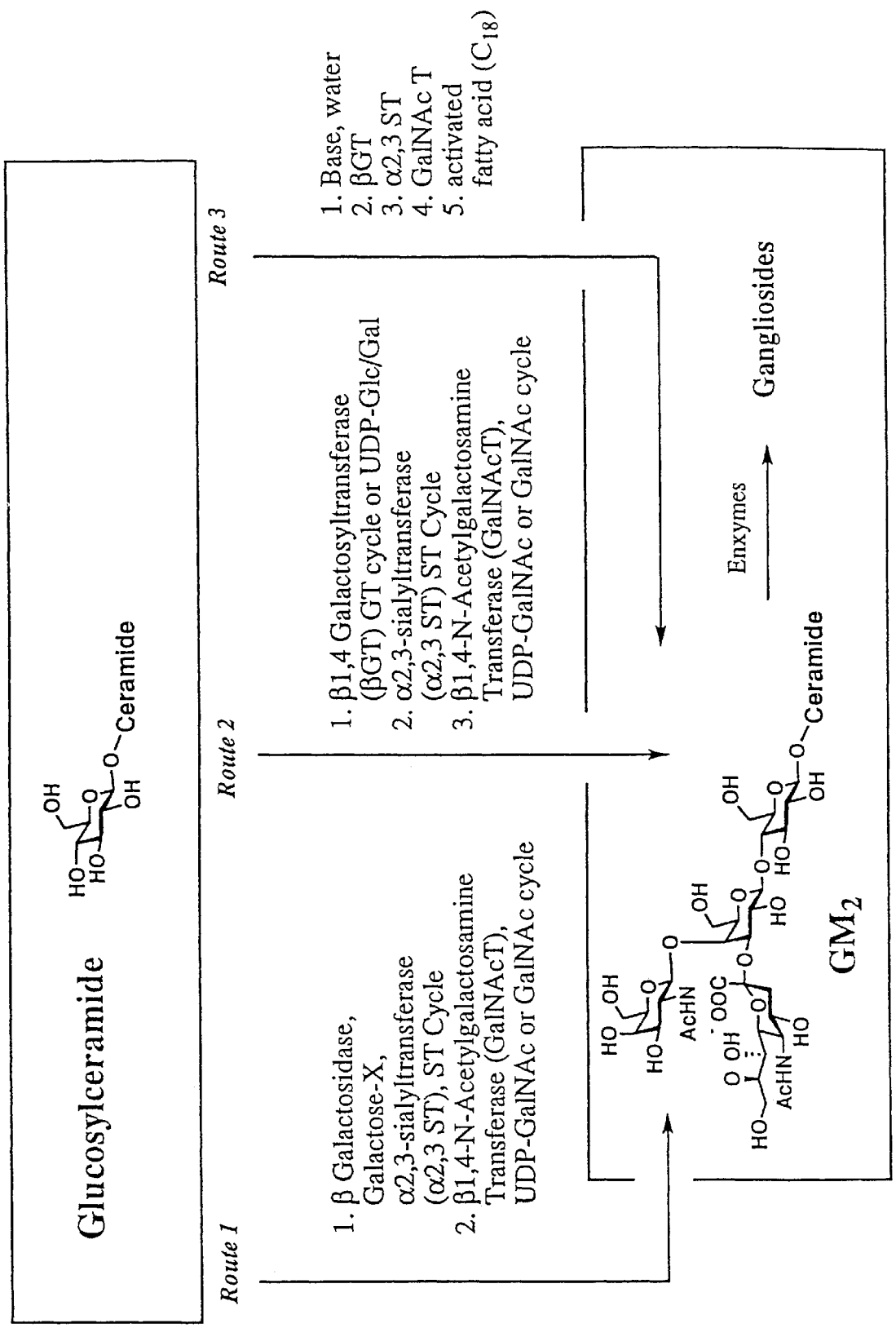
FIG. 4 shows three routes for synthesizing GM2 and other gangliosides starting from a glucosylceramide.

This Example describes three alternative procedures for the synthesis of the GM2 and other gangliosides using a glucosylceramide as the precursor (FIG. 4). In Route 1, a β1,4-galactosidase is used to catalyze the transfer of a Gal residue to the glycosylceramide. Simultaneously, an α2,3-sialyltranasferase is used in a sialyltransferase cycle to link a sialic acid residue to the Gal. Next, a β1,4-GalNAc transferase is added to the reaction mixture, either with UDP-GalNAc or as part of a GalNAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or UDP-Glc/Gal as the acceptor sugar. Sialylation and addition of GalNAc are carried out as described above to obtain GM2.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. In the example shown in FIG. 4, an activated $C_{18}$ fatty acid is used, resulting in the synthesis of GM2. Greater efficiency is generally observed when the fatty acid is removed prior to the glycosylation reactions.

After each synthetic route, additional glycosyltransferases can be used to add additional saccharide residues in order to obtain more complex gangliosides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of enzymatically synthesizing a glycosphingoid from a sphingoid, the method comprising:

(a) removing the fatty acid from the sphingoid;
   (b) contacting the product from step (a) with a glycosyltransferase reaction mixture comprising:
       i) at least one glycosyltransferase,
       ii) a corresponding nucleotide sugar for each glycosyltransferase,
       iii) other reactants required for glycosyltransferase activity; and
       iv) an organic solvent for a sufficient time and under appropriate conditions to transfer a sugar from said nucleotide sugar to the product from step (a), thereby forming said glycosphingoid.

2. The method of claim 1, wherein the method further comprises:

(c) attaching a fatty acid to said glycosphingoid.

3. The method of claim 1, wherein the sphingoid has the formula I:

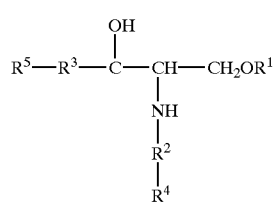

wherein
$R^1$ is selected from the group consisting of H, Glcβ1-, Galβ1-, and lactoseβ1-;
$R^2$ is selected from the group consisting of $CH_2$ and

$R^3$ is selected from the group consisting of

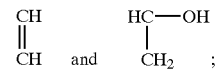

$R^4$ is selected from the group consisting of:
(i) $C_2$–$C_{36}$ saturated, unsaturated, or polyunsaturated alkyl;
(ii) α-hydroxy-$C_2$–$C_{36}$ alkyl;
(iii) ω-hydroxy-$C_2$–$C_{36}$ alkly;
(iv) α, ω-dihydroxy-$C_2$–$C_{36}$ alkyl; and
(v) an alkanoyl group having the formula:

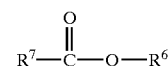

in which $R^6$ is either a divalent $C_2$–$C_{36}$ alkyl or divalent α-hydroxy-$C_2$–$C_{36}$ alkyl, and $R^7$ is either a monovalent $C_2$–$C_{36}$ alkyl or monovalent α-hydroxy-$C_2$–$C_{36}$ alkyl; and
$R^5$ is selected from the group consisting of a saturated, unsaturated, or polyunsaturated $C_2$–$C_{37}$ alkyl group.

4. The method of claim 1, wherein said sphingoid has the comprises a formula:

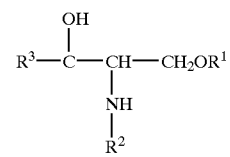

wherein $R^1$ is selected from the group consisting of H, Glcβ1-, Galβ1-, lactoseβ1-, and an oligosaccharide;
$R^2$ is selected from the group consisting of H and a saturated or unsaturated $C_2$–$C_{26}$ alkyl group, and a protecting group; and
$R^3$ is a saturated, unsaturated, or polyunsaturated $C_2$–$C_{37}$ alkyl group, or a protecting group.

5. The method of claim 1, wherein the sphingoid is a ceramide.

6. The method of claim 1, wherein the sphingoid comprises one or more saccharide residues.

7. The method of claim 1, wherein the method further comprises removal of one or more saccharide residues from said sphingoid prior to contacting said sphingoid with the glycosyltransferase reaction mixture.

8. The method of claim 1, wherein the sphingoid is selected from the group consisting of:
   a) ceramide (Cer);
   b) Glcβ1-Cer;
   c) Galβ1-Cer;
   d) Gal4Glcβ1-Cer;
   e) Neu5Ac3Gal4GlcCer;
   f) GalNAc4(Neu5Ac3)Gal4GlcCer;
   g) Neu5Ac3Gal3GalNAc4Gal4GlcCer;

h) Neu5Ac8Neu5Ac3Gal4GlcCer;

i) GalNAc4(Neu5Ac8Neu5Ac3)Gal4GlcCer;

j) Neu5Ac3Gal3GalNAc4(Neu5Ac3)Gal4GlcCer;

k) Neu5Ac3Gal3(Neu5Ac6)GalNAc4Gal4GlcCer;

l) Gal3GalNAc4(Neu5Ac8Neu5Ac3)Gal4GlcCer;

m) Neu5Ac8Neu5Ac3Gal3GalNAc4(Neu5Ac3)Gal4GlcCer;

n) Neu5Ac3Gal3GalNAc4(Neu5Ac8Neu5Ac3)Gal4GlcCer;

o) Gal3GalNAc4(Neu5Ac8Neu5Ac8Neu5Ac3)Gal4GlcCer; and p) Neu5Ac8Neu5Ac3Gal3GalNAc4(Neu5Ac8Neu5c3)Gal4GlcCer.

9. The method according to claim 1, wherein the glycosyltransferase is a β-1,4-galactosaminyl transferase and the nucleotide sugar is UDP-GalNAc.

10. The method according to claim 9, wherein said sphingoid is selected from GM3 and GD3.

11. The method according to claim 10, further comprising contacting the product from step (a) with a second glycosyltransferase, which is a β-1,3-galactosyl transferase and a second nucleotide sugar, which is UDP-Gal.

12. The method according to claim 11, further comprising contacting the product from step (a) with a second sphingoid.

13. The method according to claim 12, wherein said second sphingoid is a member selected from GM2 and GD2.

14. The method of claim 1, wherein the sphingoid is Neu5Ac3Gal4GlcCer, the glycosyltransferase is a β1,4-GalNAc transferase, the nucleotide sugar is UDP-GalNAc and the product is GalNAc4Neu5Ac3Gal4GlcCer.

15. The method of claim 14, wherein the Neu5Ac3Gal4GlcCer is produced using a method that comprises contacting Gal4GlcCer with an α2,3-sialyltransferase and CMP-Neu5Ac.

16. The method of claim 15, wherein the Gal4GlcCer is produced using a method that comprises contacting GlcCer with a β1,4-galactosyltransferase and UDP-Gal.

17. The method of claim 16, wherein the GlcCer is a plant glycosylceramide.

18. The method of claim 1, wherein the sphingoid is Neu5Ac8Neu5Ac3Gal4GlcCer, the glycosyltransferase is a β1,4-GalNAc transferase, the nucleotide sugar is UDP-GalNAc and the product is GalNAc4(Neu5Ac8Neu5Ac3)Gal4GlcCer.

* * * * *

UNITED STATES PATENT AND TRADEMARK OFFICE
CERTIFICATE OF CORRECTION

PATENT NO. : 6,440,703 B1
DATED : August 27, 2002
INVENTOR(S) : Shawn DeFrees

It is certified that error appears in the above-identified patent and that said Letters Patent is hereby corrected as shown below:

Column 23,
Lines 34-35, delete "glycosphingod" and insert therefor -- glycosphingoid --.

Column 24,
Line 34, delete "comprises a".
Line 53, delete "sacchanide" and insert therefor -- saccharide --.

Signed and Sealed this

Eleventh Day of March, 2003

JAMES E. ROGAN
*Director of the United States Patent and Trademark Office*